United States Patent
Nelson

(10) Patent No.: US 7,220,858 B2
(45) Date of Patent: May 22, 2007

(54) SYNTHESIS OF HYDRAZINE AND CHLORINATED DERIVATIVES OF BICYCLIC PYRIDAZINES

(75) Inventor: Deanna J. Nelson, Cary, NC (US)

(73) Assignee: Barbeau Pharma, Inc., Northfield, IL (US)

( * ) Notice: Subject to any disclaimer, the term of this patent is extended or adjusted under 35 U.S.C. 154(b) by 319 days.

(21) Appl. No.: 10/745,230

(22) Filed: Dec. 23, 2003

(65) Prior Publication Data

US 2005/0137397 A1  Jun. 23, 2005

(51) Int. Cl.
*C07D 237/30* (2006.01)

(52) U.S. Cl. ..................................... 544/237
(58) Field of Classification Search ............... None
See application file for complete search history.

(56) References Cited

U.S. PATENT DOCUMENTS 2,484,029 A * 10/1949 Hartmann et al. .......... 260/250

FOREIGN PATENT DOCUMENTS

JP    2001-172248    *  6/2001

OTHER PUBLICATIONS

Druey and Ringier, "Hydrazinderivate der Phtalazin- und Pyridazinreihe" Helvetica Chimica Acta, vol. 34(21), pp. 195-210 (1951).*
Sycheva et al, "Synthesis of Apressine" Meditsinskaya Promyshlennost SSSR, vol. 14(2), pp. 13-17 (1960) Caplus Abstract.*
Butula et al, "Eine neue Methode zur Gewinnung von 1-Hydrazino-phthalazin" Croatica Chemica Acta, vol. 52(1), pp. 43-45 (1979).*

* cited by examiner

*Primary Examiner*—James O. Wilson
*Assistant Examiner*—Zachary C. Tucker
(74) *Attorney, Agent, or Firm*—Schiff Hardin LLP

(57) ABSTRACT

The present invention relates to both a novel method of preparing hydralazine hydrochloride and to a novel method of preparing hydrazine derivatives of compounds containing a pyridazine ring, including, for example, pyridazines, phthalazines and other compounds containing the pyridazine ring.

14 Claims, 6 Drawing Sheets

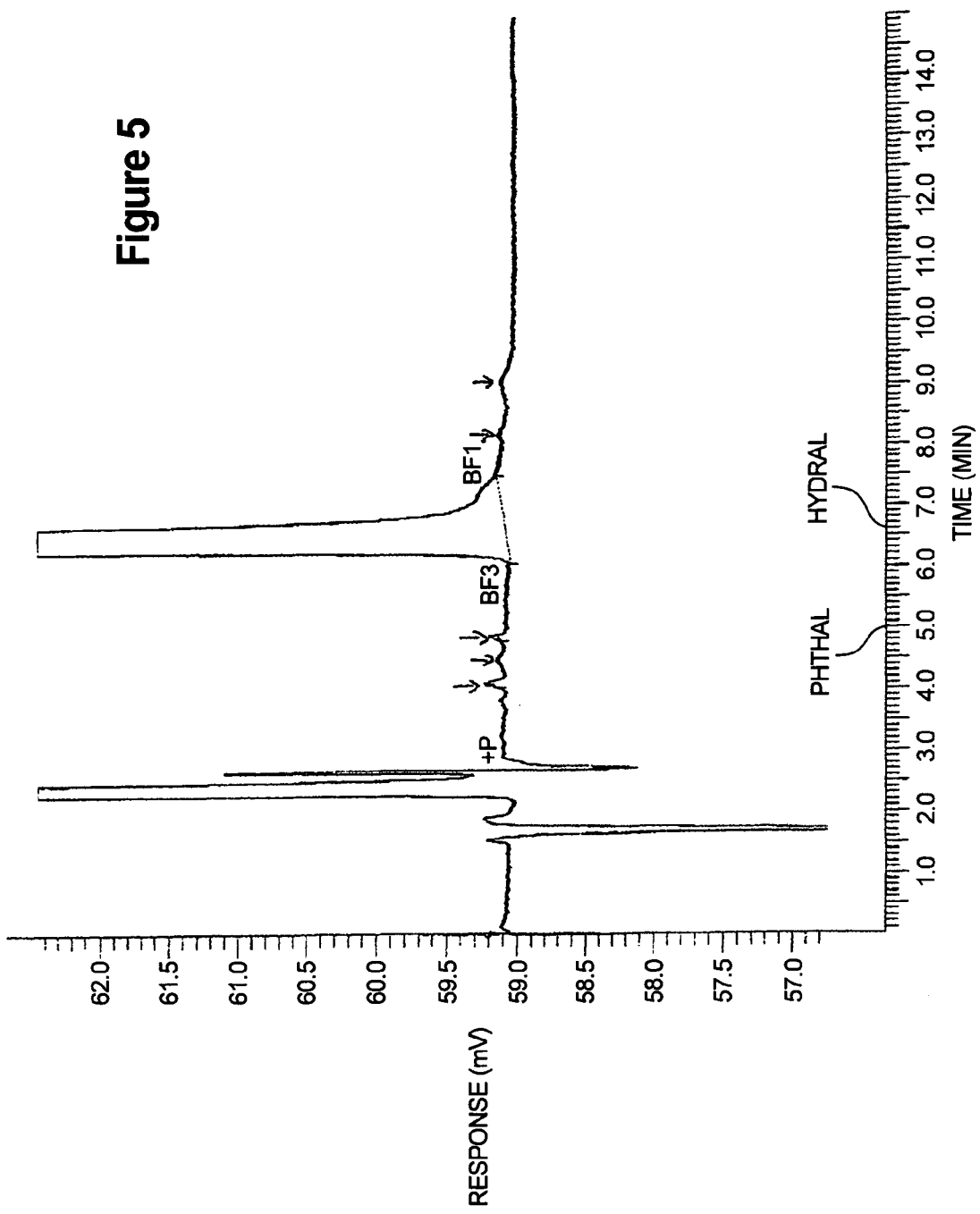

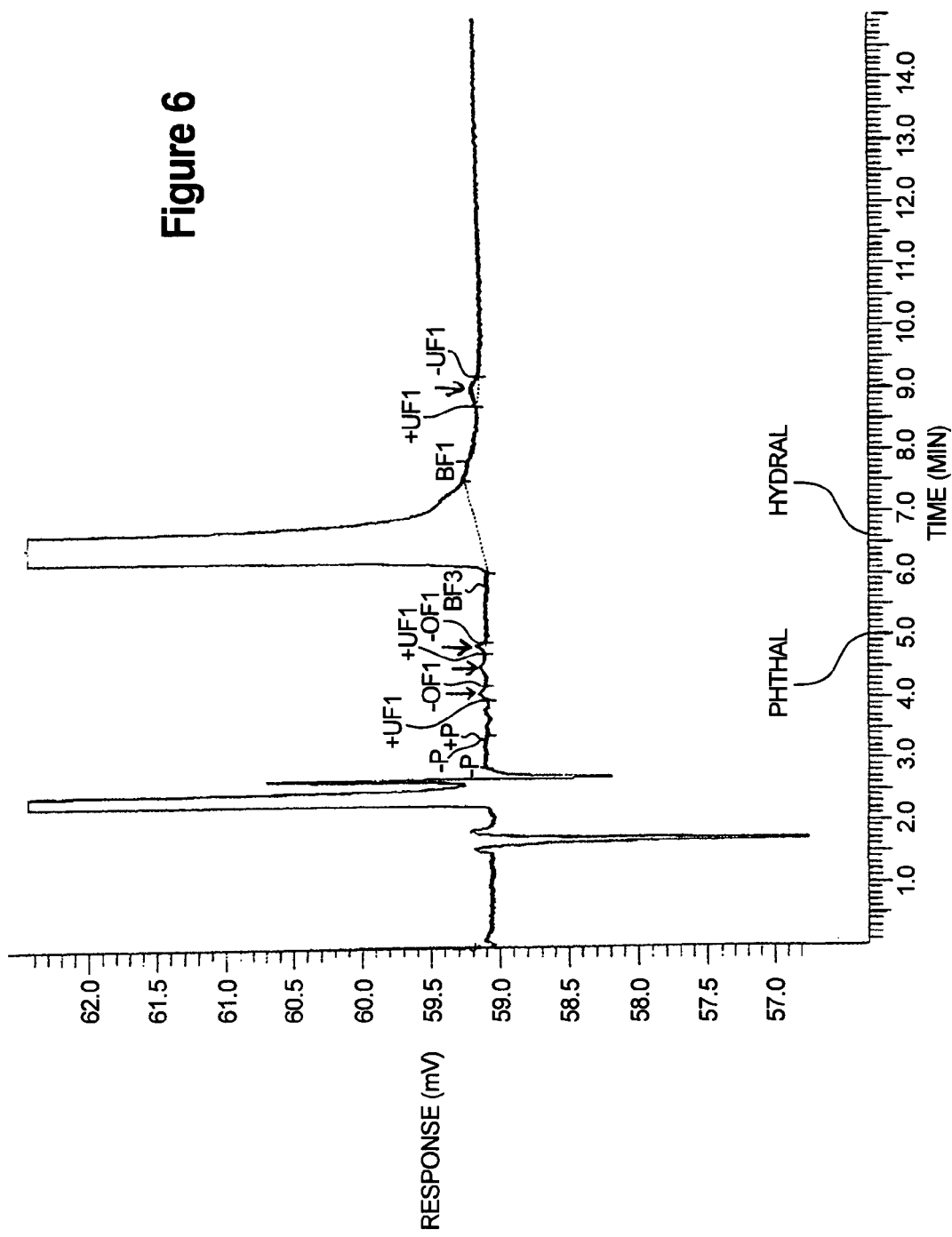

SYNTHESIS OF HYDRAZINE AND CHLORINATED DERIVATIVES OF BICYCLIC PYRIDAZINES

BACKGROUND OF THE INVENTION

The present invention relates to both a novel method of preparing hydralazine hydrochloride and to a novel method of preparing hydrazine derivatives of compounds containing a pyridazine ring, including, for example, pyridazines, phthalazines and other compounds containing the pyridazine ring.

Hydralazine hydrochloride is a peripheral vasodilator that was discovered about 50 years ago. Hydralazine exerts an antihypertensive effect directly on vascular smooth muscle, producing relaxation of muscle fibers resulting in a decrease in blood pressure. Hydralazine, is an artery-specific direct peripheral vasodilator having an onset of action between 10–30 minutes (10–20 minutes given intravenously), a maximum hypotensive effect in 10–80 minutes, and duration of action between 3–4 hours. Hydralazine is extensively metabolized in the body to products that are excreted predominantly in the urine, and undergoes N-acetylation, oxidation, hydroxylation, hydrazone formation, and conjugation. Hydralazine is one of the few injectable antihypertensive drugs that maintain blood flow to kidneys during hypertensive crisis, and the only one to increase blood flow to an already compromised kidney.

Over 60 million people in the United States suffer from essential hypertension. About 1% of these people suffers from hypertensive crisis and requires hospital-based acute care. Of the hypertensive crisis patients, 76% are "urgencies" and 24% "emergencies" with end-organ damage. Hypertensive crisis, however, is a medical emergency that requires immediate therapy for certain patients in hospital emergency rooms, operating rooms, and intensive care units. Hypertensive crisis is a life-threatening situation, and includes hypertensive emergencies and hypertensive urgencies characterized by acute elevations in blood pressure that must be brought under control within hours.

A particularly troubling group of patients with hypertensive crisis are women with pregnancy-induced hypertension. Pregnancy induced hypertension complicates 7% to 10% of the estimated 6.2 million pregnancies in the United States each year and is considered a major cause of maternal and fetal morbidity and mortality. These complications vary from mild to severe pre-eclampsia and eclampsia. Severe pre-eclampsia, which occurs in approximately 10% of pre-eclamptic patients, usually occurs after 20 weeks gestation and is determined by levated blood pressures of 140/90 mm Hg or greater. It is characterized by hypertension, proteinuria, generalized edema and disturbances in coagulation and liver function. Pre-eclampsia can progress to eclampsia, a convulsive disorder that can cause cerebral hemorrhage and maternal death. Complications resulting from pre-eclampsia and eclampsia are a major cause of maternal deaths around the world, and account for about 17% of maternal deaths in the United States. About half of these deaths in the United States are due to cardiovascular and central nervous system complications, including hemorrhage and embolism. Moreover, in women without proteinuria, the risk of fetal death rises more than three-fold from 6.2/1000 if the diastolic blood pressure is 75–84 mmHg to 19.2/1000 if the diastolic blood pressure is 104 mmHg.

Hydralazine hydrochloride is commercially available in both oral tablet and sterile injectable dosage forms. The sterile injectable form is used to lower blood pressure primarily in pregnant women suffering from severe preeclampsia and eclampsia in hypertensive crisis situations. The oral tablet form of hydralazine hydrochloride is used in patients requiring long-term management of their hypertension after such a crisis has abated. Hydralazine hydrochloride is very unstable in all of the sterile injectable pharmaceutical formulations currently available. Continuing instability problems with injectable hydralazine hydrochloride, for example, have plagued pharmaceutical manufacturers for many years, forcing these companies to remove their injectable hydralazine products from the marketplace. In all current embodiments of its injectable formulations, hydralazine hydrochloride forms small yellow-green particles following storage from 1 to about 2 months when hydralazine is stored at 40° C. and after from 6 to about 9 months storage at 25° C. Although the identification of the yellow-green particles has yet to be confirmed, it is believed that the particles are insoluble polymeric products formed by reaction of hydralazine and contaminating by-products of hydralazine manufacture during storage of hydralazine solutions.

Despite its unique pharmacologic properties as an antihypertensive drug, the therapeutic use of hydralazine hydrochloride has been limited by its instability during storage. A stable hydralazine pharmaceutical composition that is more easily manufactured and does not degrade or produce particulate matter during extended storage of the bulk drug substance or its formulations does not currently exist. Moreover, a method of manufacture of hydralazine hydrochloride that provides a pharmaceutical quality product that is free of contaminating by-products such as hydrazine, metal ions, or chlorinated pyridazine-containing compounds is not currently available.

A conventional method of manufacture that is widely used for the commercial manufacture of hydralazine hydrochloride is disclosed in U.S. Pat. No. 2,484,029 to M. Hartmann and J. Druey. According to Hartmann and Druey, hydrazine derivatives of pyridazine compounds are formed by reacting a hydrazine with a pyridazine compound of the desired structure but containing a group in the ortho position to a ring nitrogen that is replaceable by a hydrazine radical. Examples of such replaceable groups are a halogen, an esterified hydroxyl group, or an aryloxy or thioether group. Compounds containing the pyridazine ring that may be used as starting materials are substituted or unsubstituted compounds including 1-chlorophthalazine, 1-chloro-4-methylphthalazine, 1-chloro-4-ethylphthalazine, 1-chloro-4-propylphthalazine, 1-chloro-4-butylphthalazine, 1-chloro-4-benzylphthalazine, 1-chloro-7-methoxyphthalazine, 1-chloro-7,8-dimethoxyphthalazine, 1-chloro-6-hydroxyphthalazine, 1-chloro-4-phenylphthalazine, 1-chloro4-(p-methoxyphenyl)phthalazine, 1,4-dichlorophthalazine, 3-chloropyridazine, 3-chloro-6-methylpyridazine, 3-chloro-6-phenylpyridazine, 3-chloro-6(p-hydroxyphenyl)pyridazine, 6-chloro-3-phenylpyrido-2',3',4,5-pyridazine, and 6-chloro-3-phenylpyrido-3',4',4,5-pyridazine. Insofar as the starting materials such as the phthalazines or pyridazines are not known, they can be obtained from corresponding oxo-carboxylic acids by reaction with hydrazine. The oxo compounds, for example, the phthalazones or pyridazones thus obtained, may be converted into their chlorine compounds, for example, by treatment with phosphorus oxychloride. As hydrazines, hydrazine itself or its substitution products wherein a nitrogen atom may form part of a ring, as, for example, morpholine or piperidine, may be employed. Examples of suitable hydrazines are: hydrazine, methylhydrazine, benzylhydrazine, asymmetrical dimethylhydrazine, symmetrical dimethylhydrazine, propylhydrazine, allylhydrazine, N-methyl-N-butylhydrazine, N-aminopiperidine, N-aminomorpholine, 3-methyl-cyclohexylhydrazine, and the like. Also, these hydrazines may be employed in the form of their salts. The conversion with hydrazines is carried out suitably in the presence of diluents, if desired also in the presence of condensing agents, and if desired in the presence of catalysts such as copper powder.

According to the method of manufacture of U.S. Pat. No. 2,484,029, 1-chlorophthalazone is prepared by treating 30 parts by weight of 1-phthalazinone with phosphorus oxychloride as described in Berichte des Deutsche Chemische Gesellschaft, vol. 26, page 521, 1893. The freshly obtained yet moist chloro compound is heated on a water bath for two hours in a mixture of 100 parts by volume of ethyl alcohol and 90 parts by volume of hydrazine hydrate. The hot solution is filtered, and hydralazine crystallizes out in yellow needles on cooling. It is filtered with suction and washed with cold ethyl alcohol. The compound is crystallized from methyl alcohol. On warming in alcoholic or aqueous hydrochloric acid, hydralazine hydrochloride is obtained.

When manufactured according to the methods of manufacture of U.S. Pat. No. 2,484,029, the product, hydralazine hydrochloride bulk solid, is known to contain residuals from the manufacturing process including, for example, hydrazine, chlorinated or chlorophosphorylated phthalazine or pyridazine intermediates, and phthalazone or pyridazone precursors to the chlorophthalazine or chloropyridazine raw material. In addition, if copper powder was employed as a catalyst, the product, hydralazine hydrochloride bulk solid, also contains low concentrations of copper ion ($Cu^{+2}$).

Because hydrazine is a very toxic chemical, human exposure to hydrazine is severely restricted. Thus, the U.S. Pharmacopeia Official Monograph for hydralazine hydrochloride, for example, requires that pharmaceutical quality hydralazine hydrochloride contain no more than 0.1% hydrazine by weight.

Hydralazine is known to chelate metal ions. Sinha and Motten [Biochemical and Biophysical Research Communications 105(3): 1044–1051 (1982)] report that hydralazine oxidizes rapidly in the presence of oxygen and metal ions such as $Cu^{+2}$, $Fe^{+2}$, and $Fe^{+3}$ through free radical intermediates in a manner similar to other hydrazine derivatives.

When manufactured according to conventional methods of manufacture, hydralazine hydrochloride undergoes degradation during storage to intensely colored, insoluble polymeric products. The numerous degradation products that form during storage have not been completely identified and characterized chemically, but it is believed that they are the products of reactions such as chelation with metal ions, oxidation, reaction of residual hydrazine raw material with chlorinated intermediates that were incompletely removed during manufacturing, and reaction of hydralazine with chlorinated intermediates that were incompletely removed during manufacturing.

It is an object of the present invention to manufacture hydralazine hydrochloride of high pharmaceutical quality that is free of contaminating by-products.

It is an object of the present invention to manufacture hydralazine hydrochloride of high pharmaceutical quality that is free of contaminating by-products such as hydrazine, metal ions, or chlorinated pyridazine-containing compounds.

It is a further object of the present invention to manufacture a stable pharmaceutical formulation of hydralazine hydrochloride that is free of contaminating by-products such as hydrazine, metal ions, or chlorinated pyridazine-containing compounds.

It is a further object of the present invention to manufacture a stable hydralazine hydrochloride pharmaceutical composition that does not degrade or produce particulate matter during extended storage of the bulk drug substance or its liquid formulations.

It is a further object of the present invention to manufacture a stable injectable pharmaceutical formulation containing hydralazine hydrochloride that has no visible particulate matter for a time more than 30 months after manufacture.

It is a further object of the present invention to manufacture a stable injectable pharmaceutical formulation containing hydralazine hydrochloride that has less than 6000 10 micron particles per container or 600 25 micron particles per container for a time more than 30 months after manufacture.

It is a further object of the present invention to produce hydralazine hydrochloride that is stable in sterile injectable pharmaceutical formulations.

BRIEF DESCRIPTION OF THE DRAWINGS

FIG. 5 is an HPLC chromatogram of hydralazine hydrochloride that was prepared conventionally. An arrow indicates the presence of each impurity peak.

FIG. 6 is an HPLC chromatogram of hydralazine hydrochloride that was prepared in accordance with the present invention. An arrow indicates the presence of each impurity peak.

BRIEF SUMMARY OF THE INVENTION

Figure 1:
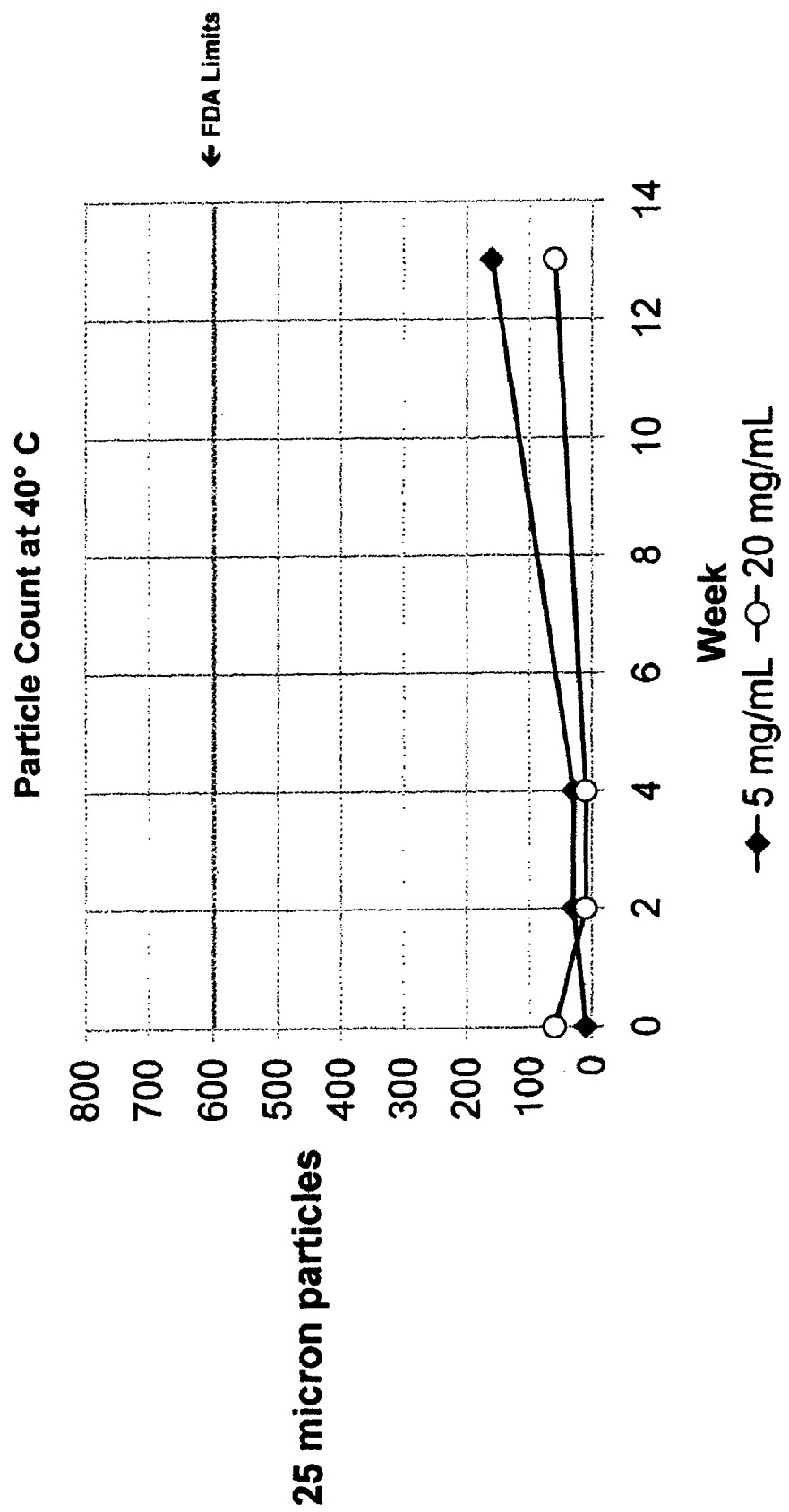
FIG. 1 is a graph of the subvisible particle count for the 25 micron particles for each of the hydralazine hydrochloride solutions for prepared in Examples 4–7 stored at 40° C. for up to 118 days.

In accordance with the present invention, disclosed is a method of preparing hydralazine hydrochloride, comprising the steps of:
  a. heating a first mixture of 1-phthalazinone with phosphorous oxychloride thereby providing 1-chlorophthalazine;
  b. contacting said 1-chlorophthalazine with an alkane having from about 5 to about 7 carbon atoms;
  c. removing said alkane from said 1-chlorophthalazine;
  d. contacting said 1-chlorophthalazine obtained in step c with tetrahydrofuran;
  e. removing said tetrahydrofuran from said 1-chlorophthalazine;
  f. heating a second mixture containing 1-chlorophthalazine from step e and hydrazine hydrate thereby providing hydralazine;
  g. separating said hydralazine from said second mixture; and h. contacting said hydralazine from step g with hydrochloric acid thereby providing hydralazine hydrochloride.

In accordance with a specific embodiment of the present invention, disclosed is a method of preparing a chlorinated heterocyclic compound having the formula:

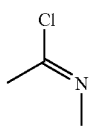

(1)

comprising the steps of:
a. heating a first mixture of a compound having the formula:

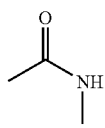

(2)

with phosphorous oxychloride thereby providing an admixture containing said chlorinated heterocyclic compound;
b. contacting said admixture with an alkane having from about 5 to about 7 carbon atoms;
c. removing said alkane from said compound 1.

DETAILED DESCRIPTION OF THE INVENTION

The method of preparing hydrazine derivatives according to the present invention comprises essentially two steps. In the first step, stable chlorinated heterocyclic compounds are prepared by the reaction of phosphorous oxychloride with compounds having the formula:

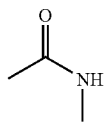

(2)

In the second step, highly purified hydrazine derivatives are prepared by the reaction of hydrazines with the stable chlorinated heterocyclic compounds having the formula:

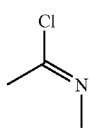

(1)

Unlike the methods of the prior art, the method of the present invention provides highly purified hydrazine derivatives in large part because these stable chlorinated heterocyclic intermediates.

In accordance with one embodiment of the present invention, representative pyridazine compounds used as the starting materials that are to be converted into their stable chlorinated heterocyclic compounds by treatment with phosphorus oxychloride include substituted and unsubstituted pyridazine-3-ones having a typical structure

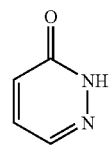

2H-Pyridazin-3-one

In accordance with another embodiment of the present invention, representative phthalazine compounds used as the starting materials that are to be converted into their stable chlorinated heterocyclic compounds by treatment with phosphorus oxychloride include substituted and unsubstituted heterocyclic compounds having the structure

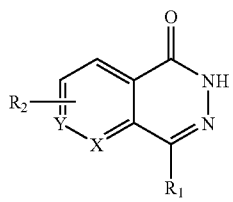

where X and Y are independently carbon or nitrogen, and $R_1$ and $R_2$ are independently selected from the group consisting of hydrogen, alkyl ($C_1$–$C_6$), alkoxy, aryl (phenyl), heteroaryl (pyrimidinyl), alkylaryl, aryloxy, and alkylaryoxy.

In accordance with yet another embodiment of the present invention, representative phthalazine compounds used as the starting materials that are to be converted into their stable chlorinated heterocyclic compounds by treatment with phosphorus oxychloride include substituted and unsubstituted heterocyclic compounds having the structure

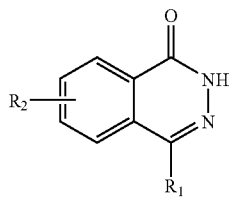

where $R_1$ and $R_2$ are independently selected from the group consisting of hydrogen, alkyl ($C_1$–$C_6$), alkoxy, aryl (phenyl), heteroaryl (pyrimidinyl), alkylaryl, aryloxy, and alkylaryoxy.

Specific examples of the substituted heterocyclic compounds include 4-Methyl-2H-phthalazin-1-one; 7-Methoxy-2H-phthalazin-1-one; and 4-(4-Methoxy-phenyl)-2H-phthalazin-1-one.

In accordance with the present invention, the stable chlorinated heterocyclic intermediates are prepared by contacting an admixture of the chlorinated heterocyclic compounds produced in the first step with an alkane having from about 5 to about 7 carbon atoms and removing the alkane. Partitioning the chlorinated heterocyclic intermediates between the admixture and the alkane provides the production of stable, free-flowing powder chlorinated heterocyclic compounds.

In a preferred embodiment of the present invention, highly purified hydralazine hydrochloride is prepared from 1-phthalazinone by heating a first mixture of 1-phthalazinone with phosphorous oxychloride thereby providing 1-chlorophthalazine, contacting said 1-chlorophthalazine with an alkane having from about 5 to about 7 carbon atoms, removing said alkane from said 1-chlorophthalazine and contacting the 1-chlorophthalazine with tetrahydrofuran. Advantageously, this embodiment of the present invention uses $POCl_3$, and removes excess $POCl_3$ and other undesired by-products without use of bases. After removing the tetrahydrofuran, the 1-chlorophthalazine is heated in a second mixture with hydrazine hydrate. The hydralazine compound produced is separated from this second mixture and converted to hydralazine hydrochloride with hydrochloric acid.

In a more preferred embodiment of the present invention, the alkane having from about 5 to about 7 carbon atoms is hexane.

In a more preferred embodiment the method of the present invention is performed in vessels having a non-metallic contact surface.

In a more preferred embodiment of the present invention, the first mixture is heated to a temperature from about 70° to about 85° C. for a time sufficient to convert 1-phthalazinone to 1-chlorophthalazine.

In a more preferred embodiment of the present invention, th second mixture is prepared by adding 1-chlorophthalazine to said hydrazine prior to heating. In a most preferred embodiment of the present invention, the said second mixture is heated to a temperature from about 60° to about 70° C. for a time sufficient to convert 1-chlorophthalazine to hydralazine.

In the most preferred embodiment of the present invention, the alkane is hexane, the first mixture is heated to a temperature from about 70° to about 85° C. for a time sufficient to convert 1-phthalazinone to 1-chlorophthalazine, and the second mixture is prepared by adding 1-chlorophthalazine to said hydrazine prior to heating at a temperature from about 60° to about 70° C. for a time sufficient to convert 1-chlorophthalazine to hydralazine.

Hydralazine hydrochloride compositions prepared in accordance with the synthetic method of the present invention are surprisingly highly pure and essentially free of phthalazines, hydrazine and metal ions that are normally found in stainless steel resulting in a stable active pharmaceutical ingredient. In accordance with the present invention, the terms "essentially free of phthalazine compounds" or "essentially free of phthalazines" refers to compositions comprising less than about 1% by weight of phthalazine compounds. In a more preferred embodiment of the present invention, hydralazine hydrochloride compositions comprise less than about 0.5% by weight of phthalazine compounds. In accordance with the present invention, the terms "essentially free of hydrazine compounds" or "essentially free of hydrazines" refers to compositions comprising less than about 0.0005% by weight of hydrazine compounds.

In accordance with the present invention, the terms "essentially free of metal ions" refers to compositions comprising less than about 15 parts per million of metal ions. In a more preferred embodiment of the present invention, hydralazine hydrochloride compositions comprise less than about 10 parts per million metal ions. The individual metal ions are selected from the group consisting of copper ions, iron ions, manganese ions, nickel ions, molybdenum ions, and cobalt ions. In accordance with the present invention, the concentration of the individual metal ions might vary; however, the aggregate concentration of metal ions is preferably less than about 15 parts per million and more preferably less than about 10 parts per million.

In accordance with a preferred embodiment of the present invention, the hydralazine hydrochloride compositions comprise less than 1% by weight phthalazine compounds, less than about 0.0005% by weight hydrazine, and less than about 15 parts per million metal ions. In accordance with a more preferred embodiment of the present invention, the hydralazine hydrochloride compositions comprise less than 0.5% by weight phthalazine compounds, less than about 0.0005% by weight hydrazine, and less than about 15 parts per million metal ions. In accordance with a most preferred embodiment of the present invention, the hydralazine hydrochloride compositions comprise less than 0.5% by weight phthalazine compounds, less than about 0.0005% by weight hydrazine, and less than about 10 parts per million metal ions.

In accordance with a more preferred embodiment of the present invention, reaction vessels for the preparation of hydralazine hydrochloride are constructed with solution contact surfaces that are essentially non-metallic. In accordance with a most preferred embodiment of the present invention, reaction vessels for the preparation of hydralazine hydrochloride are constructed with solution contact surfaces that are non-metallic.

The differences in the purity of hydralazine hydrochloride that was prepared in accordance with the. present invention relative to hydralazine hydrochloride prepared conventionally are shown by comparison of the HPLC chromatograms of each material (FIGS. 6 and 5, respectively). Clearly, the number of impurity peaks (shown by arrows) in hydralazine hydrochloride of the present invention is less than the number present in hydralazine hydrochloride conventionally prepared. Likewise, the intensity of each impurity peak (e.g., the peak height or area under the peak) is less in hydralazine hydrochloride of the present invention than in hydralazine hydrochloride conventionally prepared.

The synthetic method of the present invention not only provides a stable and highly purified hydralazine hydrochloride composition, it unexpectedly and surprisingly provides a stable hydralazine-containing pharmaceutical composition. In accordance with the present invention, "a stable hydralazine pharmaceutical composition" refers to one that is either manufactured without significant degradation, one that does not degrade significantly during storage or one that does not produce significant levels of particulate (visible or submicron) matter during extended storage. In accordance with the present invention, hydralazine pharmaceutical compositions include finished dosage forms such as tablets and liquids for oral administration, and liquids for parenteral administration.

Pharmaceutical compositions of the present invention suitable for parenteral administration comprise sterile aqueous injection solutions of hydralazine hydrochloride. The sterile aqueous injection solutions of the present invention preferably comprise a therapeutically effective dose of hydralazine hydrochloride in a pharmaceutically acceptable carrier or diluent in a sealed container. In accordance with one aspect of the present invention, these sterile aqueous solutions are preferably isotonic with the blood of the intended recipient.

In accordance with one aspect of the present invention, the pharmaceutical compositions comprise sterile aqueous solutions of hydralazine hydrochloride that is essentially free of phthalazines. In accordance with a preferred embodiment of the present invention, the pharmaceutical composition comprises hydralazine hydrochloride wherein the hydralazine has less than about 1% by weight of phthalazine compounds associated with it. In accordance with a more preferred embodiment of the present invention, the composition comprises hydralazine hydrochloride wherein the hydralazine has less than about 0.5% by weight of phthalazine compounds associated with it.

In accordance with another aspect of the present invention, the pharmaceutical compositions comprise sterile aqueous solutions of hydralazine hydrochloride that are essentially free of hydrazine. In accordance with a preferred embodiment of the present invention, the pharmaceutical composition comprises hydralazine hydrochloride wherein the hydralazine has less than about 0.0005% by weight of hydrazine associated with it.

In accordance with another aspect of the present invention, the pharmaceutical compositions comprise sterile aqueous solutions of hydralazine hydrochloride that are essentially free of metal ions. In accordance with a preferred embodiment of the present invention, the composition comprises hydralazine hydrochloride wherein the hydralazine has less than about 15 parts per million metal ions associated with it. In accordance with a more preferred embodiment of the present invention, the pharmaceutical composition comprises hydralazine hydrochloride wherein the hydralazine has less than about 10 parts per million metal ions associated with it.

In accordance with a more preferred embodiment of the present invention, the pharmaceutical compositions comprise sterile aqueous solutions of hydralazine hydrochloride that are essentially free of phthalazines, hydrazine and metal ions. In accordance with a most preferred embodiment of the present invention, the pharmaceutical compositions comprise sterile aqueous solutions of hydralazine hydrochloride contain less than 1% by weight of phthalazine compounds, less than 0.0005% by weight hydrazine and less than 15 parts per million metal ions.

The sterile aqueous injection solutions of the present invention preferably comprise a therapeutically effective dose of hydralazine hydrochloride, that is, an amount of hydralazine hydrochloride that is effective in lowering the blood pressure of a patient when administered. In accordance with one aspect of the present invention, the therapeutically effective dose is from about 5 to about 20 mg and the concentration of hydralazine hydrochloride is from about 5 to about 20 mg/mL. In accordance with a preferred embodiment of the present invention, the therapeutically effective dose is from about 5 to about 20 mg and the concentration of hydralazine hydrochloride is 20 mg/mL. In accordance with a most preferred embodiment of the present invention, the therapeutically effective dose is from about 5 to about 20 mg and the concentration of hydralazine hydrochloride 5 mg/mL.

The sterile aqueous injection solutions of the present invention preferably comprise a therapeutically effective dose of hydralazine hydrochloride in a pharmaceutically acceptable liquid carrier or diluent for parenteral administration to a patient. In general, water, saline, aqueous dextrose (glucose), and related sugar solutions and glycols such as propylene glycol or polyethylene glycols are suitable carriers for parenteral solutions. Suitable pharmaceutical carriers are described in Remington's Pharmaceutical Sciences, and other standard reference texts in this field. In accordance with the present invention, pharmaceutically acceptable carriers and diluents preferably include sodium chloride (saline), preservatives such as methyl- or propyl-paraben, or polyethylene glycol in sterile water for injection.

In accordance with the present invention, a preferred pharmaceutically acceptable diluent includes poly(ethylene glycol) (PEG) having an average molecular weight of 200, 400, 600, 1,000, 3,000, 5,000, or 10,000 Daltons in sterile water for injection (i.e., PEG xxxx, where "xxx" is the average molecular weight). In a more preferred embodiment of the present invention, the polyethylene glycol is "essentially free" of ethylene oxide and ethylene glycol, i.e., it meets U.S. Pharmacopeial monograph standards for absence of ethylene oxide and ethylene glycol. In a most preferred embodiment of the present invention, the pharmaceutical formulation of hydralazine hydrochloride contains 5 mg/mL hydralazine hydrochloride, 0.325 mg/mL methyl paraben, 0.175 mg/mL propyl paraben, and 100 mg/mL poly(ethylene glycol) 400 in sterile water for injection.

The sterile aqueous injection solutions of the present invention preferably comprise a therapeutically effective dose of hydralazine hydrochloride in a unit dose or mutidose container. In accordance with a preferred embodiment of the present invention, the therapeutically effective dose of hydralazine hydrochloride is provided in a sealed ampoule or vial. In accordance with a most preferred embodiment of the present invention, there is provided an injectable, stable, sterile composition comprising a compound of sterile aqueous solutions of hydralazine hydrochloride that are essentially free of phthalazines, hydrazine and metal ions in a sealed container.

ILLUSTRATIVE EXAMPLES OF THE INVENTION

Example 1

Conventional Method of Preparation of Hydralazine Hydrochloride.

A. Conventional Preparation of 1-Chlorophthalazine.

One mole equivalent (10 g) of 1(2H)-phthalazinone and 7.7 mole equivalents (82.5 g, 50.1 mL) of phosphorus oxychloride were charged into a 100-mL, 3-necked flask fitted with a temperature probe and condenser. The slurry was stirred and heated to 70° C., and then the heat source was removed. The mixture was allowed to cool to room temperature, and then was poured in portions over 500 g of ice. After the initial addition of the reaction mixture, a violent exotherm was observed, and a portion of the solution spilled over the sides of the container. Ice quenching was completed with extreme caution but without further incident.

Alternative workups were also examined. As a first alternative, after the reaction mixture reached room temperature, it was concentrated by heating at 45° C. under vacuum. The resulting yellow slurry was added in portions to 3 volumes of cold, deionized water. Once again, control of exothermic reactions that occurred during this quenching step was difficult. As a second alternative, after the reaction mixture reached room temperature, it was concentrated by heating at 45° C. under vacuum. To the resulting oily yellow paste was added 5 volumes of toluene, and the resulting biphasic solution was concentrated by heating at 45° C. under vacuum to remove the phosphorus oxychloridettoluene azeotrope. The process was repeated a second time. The resulting yellow paste solidified into an unworkable solid that was discarded. As a third alternative, after the reaction mixture reached room temperature, it was concentrated by heating at 45° C. under vacuum. To the resulting oily yellow paste was added 2 volumes of toluene, and the resulting biphasic solution was concentrated by heating at 45° C. under vacuum to remove the phosphorus oxychloride/toluene azeotrope. The process was repeated a second time, and then 2 volumes of tetrahydrofuran were added. The resulting slurry was stirred and cooled to 0° C. and then was filtered to isolate a light yellow solid. The filtrate was treated as described in the following paragraph.

The aqueous mixture was rendered basic by the addition of 5 N sodium hydroxide solution. A light yellow precipitate formed. The solid was isolated by extraction into dichloromethane and concentration of the resulting extracts to dryness. A moist cake of 1-chlorophthalazine was thus obtained in yields that ranged from 80% to 440% of theoretical. If the moist cake was allowed to dry, or if this material was not used immediately, it darkened and underwent degradation to a mixture of the desired product, 1-chlorophthalazine, and multiple by-products. To prevent this loss and contamination, freshly obtained, moist chloro compound was used immediately.

B. Conventional Preparation of Hydralazine.

A solution was prepared to contain 1 part by weight 1-chlorophthalazine, 100 parts by volume of ethyl alcohol and 90 parts by volume of hydrazine hydrate. It was heated for two hours and then filtered. On cooling, 1-hydrazinophthalazine (hydralazine) precipitated from the filtrate as yellow needles, which were isolated by filtration and washed with cold ethyl alcohol. The product was precipitated from methyl alcohol. The product melted, when rapidly heated, at 172–173° C. Typical yields were 30–40%.

C. Conventional Preparation of Hydralazine Hydrochloride.

On warming in alcoholic or aqueous hydrochloric acid, hydralazine hydrochloride of melting point 273° C. (with decomposition) was obtained.

Example 2

Novel Method for the Preparation of Hydralazine Hydrochloride.

A. Novel Preparation of 1-Chlorophthalazine.

One mole equivalent (250 g) of 1(2H)-phthalazinone and 3.8 mole equivalents (775 g) of phosphorus oxychloride were charged into a 3-L, 3-necked flask fitted with a temperature probe and condenser. The slurry was stirred and heated to 80° C., maintained at that temperature for 30 minutes, and then the heat source was removed. Thin layer chromatographic analysis indicated that conversion to 1-chlorophthalazine was complete. The mixture was allowed to cool to room temperature, and 1.6 L of hexanes was added. The resulting slurry was stirred for several minutes, and the hexane layer was decanted. Addition of hexanes and decantation was repeated two more times. Then 1.6 L of tetrahydrofuran was added; as the solution was stirred, an off-white precipitate formed. The solid was isolated by filtration and washed with 250 mL of cold tetrahydrofuran to afford an 85–100% yield of 1-chlorophthalazin, the desired product, as an off-white powder that could be dried and characterized.

B. Novel Preparation of Hydralazin.

To a 2-L, 3-necked, round-bottom flask fitted with a temperature probe and condenser were charged 700 mL of ethanol and 7.6 mole equivalents (630 mL) of hydrazine hydrate, and the solution was cooled to <10° C. One (1) mole equivalent (280 g) of 1chlorophthalazine (solid) was added in portions at a rate to maintain the solution temperature at <20° C. The solution was stirred and heated to 60–70° C. After 1 hour at temperature, the hot solution was filtered to remove any insoluble by-products, and the filtrate was cooled to 0–5° C. A light yellow solid formed in the cold solution, and was isolated by filtration and washed with cold ethanol. The resulting product, hydralazine free base, was dried to constant mass and characterized. Typical yields were in the range 77–80%. The hydralazine thus obtained could be used in the next step without purification.

C. Novel Preparation of Hydralazine Hydrochloride.

Hydralazine free base (1 part by weight) was heated in 6 to 7 parts by volume of 15% hydrochloric acid to a temperature of 70–80° C. The solution was filtered hot to remove traces of insoluble materials that were undesired by-products of the preceding step. Ethanol (6 to 7 parts by volume) was added to the filtrate. As the resulting solution cooled to ambient temperature and then further to 3–8° C., an off-white to pale yellow precipitate of the desired product, hydralazine hydrochloride, was obtained. Typical yields were 80–90%.

D. Recrystallization of Hydralazine Hydrochloride.

A single necked, round-bottom flask was charged with 1 part by weight of hydralazine hydrochloride (from the preceding step) and 6 parts (by volume) of 1% hydrochloric acid. The solution was stirred and heated to dissolve the solid, and then filtered hot, if necessary, to remove traces of colored insoluble by-products. Ethanol (6 parts by volume) was added to the hot (filtered) solution. As the resulting solution cooled, an off-white precipitate of purified hydralazine hydrochloride formed. The recrystallized, purified product was isolated by filtration and washed with fresh, cold ethanol. The desired product, pharmaceutical quality hydralazine hydrochloride, containing less than 0.5% by weight of undesired by-products, less than 5 ppm of trace metals, and no detectable residual hydrazine, was obtained in 85–100% yield. Melting point: 273.9–274.3° C. HPLC Chromatogram: FIG. 6. NMR Spectrum (DMSO) 3.45(s), 8.15 (t), 8.25 (t) and 9.7 (s) ppm.

Example 3

Preparation of Conventional Hydralazine Hydrochloride Pharmaceutical Composition.

A pharmaceutical formulation of hydralazine hydrochloride prepared in Example 1 was prepared to contain 20 mg/mL hydralazine hydrochloride, 0.65 mg/mL methyl paraben, 0.35 mg/mL propyl paraben, and 100 mg/mL propylene glycol in sterile water for injection. The formulation was packaged in a glass bottle that was closed and sealed with an elasteomeric stopper. Within hours of preparation, a flocculent yellow precipitate was observed in the solution. Within 24 hours, the amount of yellow particulate in the solution increased dramatically.

Example 4

Preparation of Stable Hydralazine Hydrochloride Pharmaceutical Composition.

A liquid pharmaceutical formulation of hydralazine hydrochloride prepared in Example 2 was prepared to contain 5 mg/mL hydralazine hydrochloride and 0.7% NaCl in sterile water for injection. The formulation was packaged in a glass bottle that was closed and sealed with an elasteomeric stopper.

Example 5

Preparation of Stable Hydralazine Hydrochloride Pharmaceutical Composition.

A liquid pharmaceutical formulation of hydralazine hydrochloride prepared in Example 2 was prepared to contain 5 mg/mL hydralazine hydrochloride, 0.1625 mg/mL methyl paraben, 0.0875 mg/mL propyl paraben, and 25 mg/mL propylene glycol in sterile water for injection. The formulation was packaged in a glass bottle that was closed and sealed with an elasteomeric stopper.

Example 6

Preparation of Stable Hydralazine Hydrochlorid Pharmaceutical Composition.

A liquid pharmaceutical formulation of hydralazine hydrochloride prepared in Example 2 was prepared to contain 5 mg/mL hydralazine hydrochloride, 0.65 mg/mL methyl paraben, 0.35 mg/mL propyl paraben, and 100 mg/mL propylene glycol in sterile water for injection. The formulation was packaged in a glass bottle that was closed and sealed with an elasteomeric stopper.

Example 7

Preparation of Stable Hydralazine Hydrochloride Pharmaceutical Composition.

A liquid pharmaceutical formulation of hydralazine hydrochloride prepared in Example 2 was prepared to contain 20 mg/mL hydralazine hydrochloride, 0.65 mg/mL methyl paraben, 0.35 mg/mL propyl paraben, and 100 mg/mL propylene glycol in sterile water for injection. The formulation was packaged in a glass bottle that was closed and sealed with an elasteomeric stopper.

Example 8

Analysis of Stable Hydralazine Hydrochloride.

Hydralazine hydrochloride was prepared as in Example 2 and subjected to chemical analysis. The results of this chemical analysis id shown in Table 1 below:

TABLE 1

Analysis of Stable Hydralazine Hydrochloride

| Analytical Test | USP Specifications | Hydralazine Hydrochloride prepared as in Example 2 |
|---|---|---|
| Hydrazine impurity | NMT 0.001% | 0.000% |
| Chromatographic Purity (impurities) | NMT 1.0% | 0.2% |
| Phthalazine impurity | None | 0.0% |
| Hydralazine content | 98–102% | 100.8% |
| Stainless Steel Metal Ions | None | 10 ppm |
| Organic volatile impurities: | | |
| Ethanol | NMT 5000 ppm | 324–479 ppm |
| Hexanes | NMT 290 ppm | Not Detected |
| Tetrahydrofuran | NMT 5000 ppm | Not Detected |

Example 9

Evaluation of Storage Stability of Hydralazine Hydrochlorid in Solutions for Pharmaceutical Administration.

Figure 2:
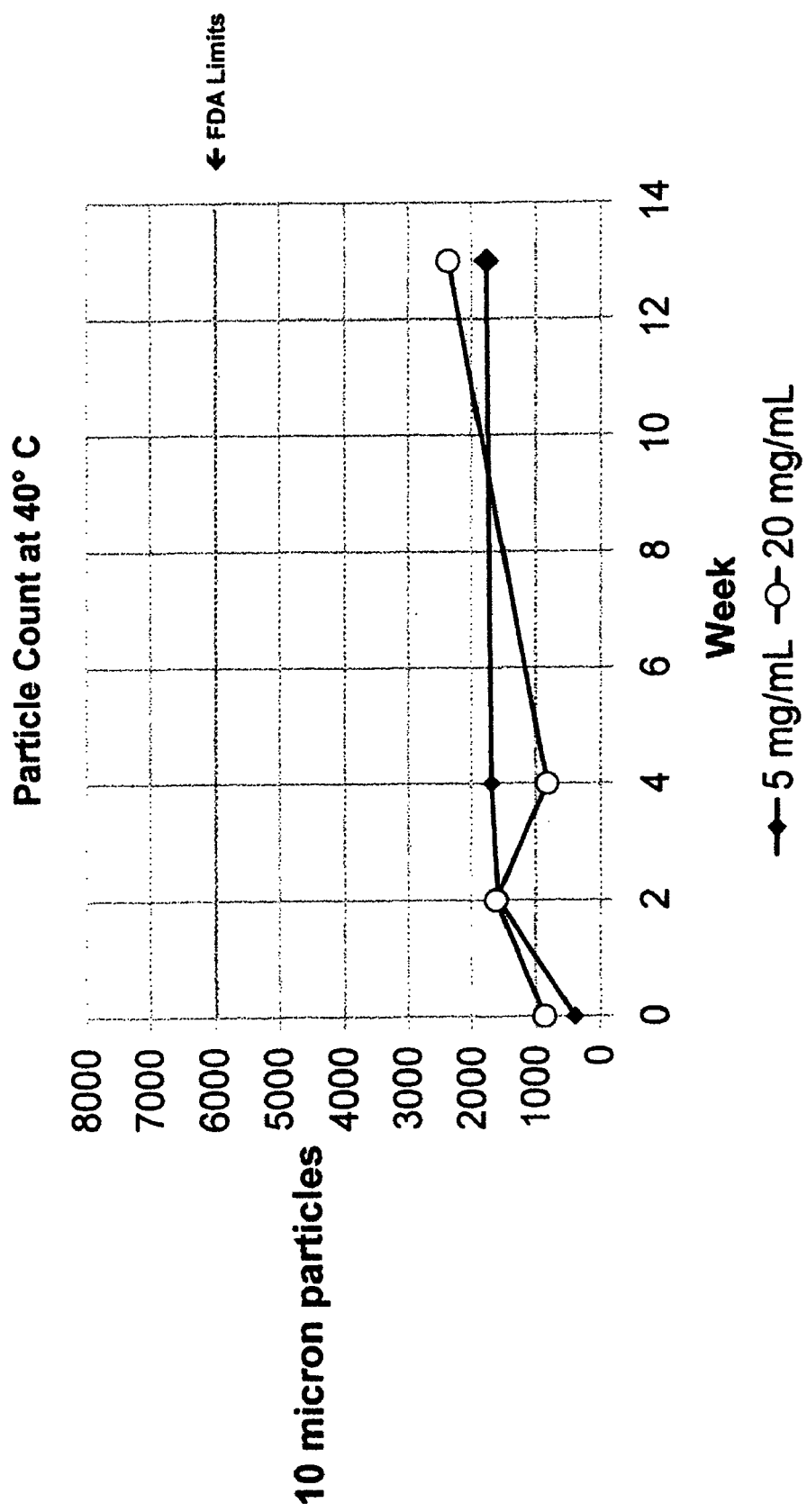
FIG. 2 is a graph of the subvisible particle count for the 10 micron particles for each of the hydralazine hydrochloride solutions for prepared in Examples 4–7 stored at 40° C. for up to 118 days.
Figure 3:
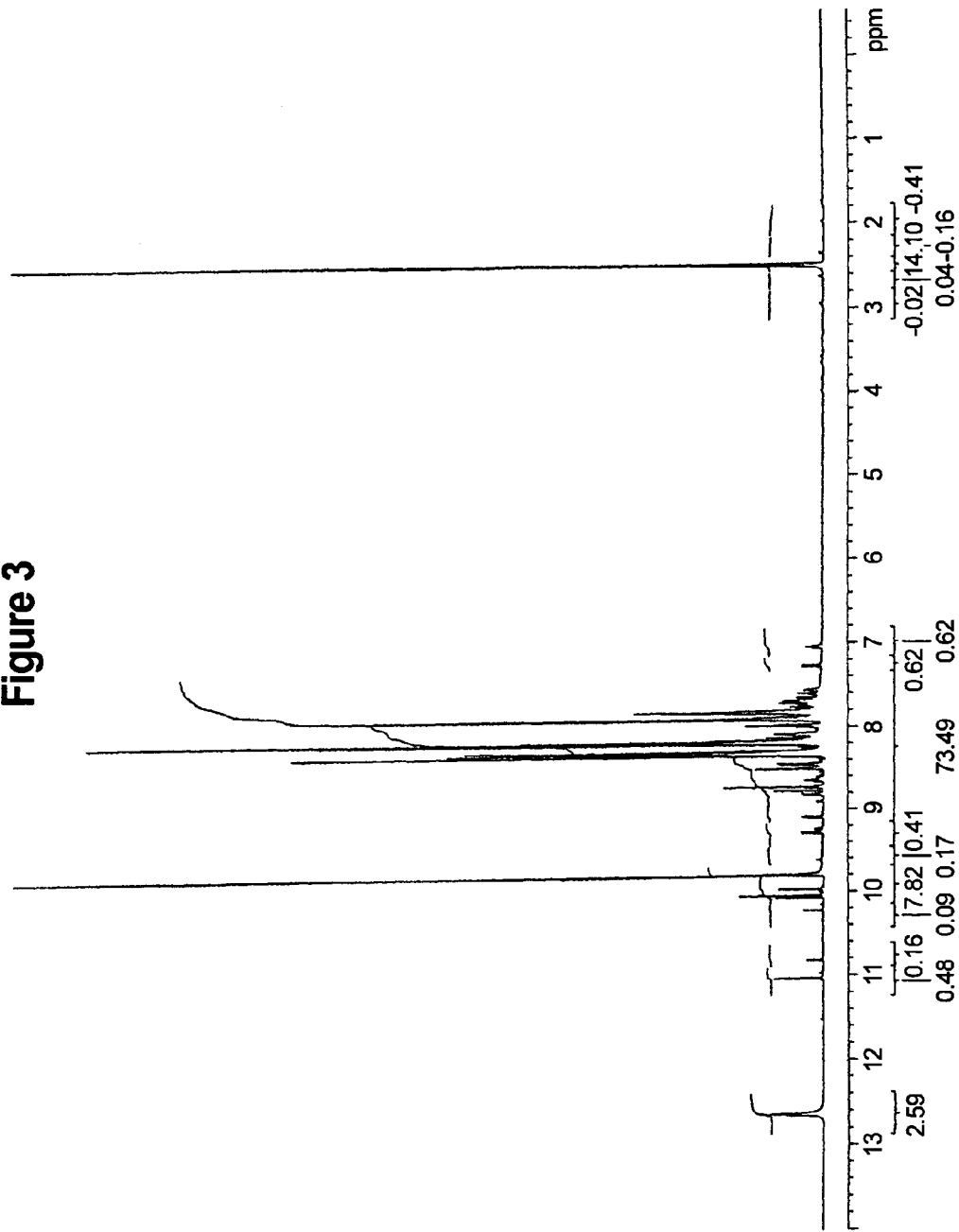
FIG. 3 is a $^1H$ nuclear magnetic resonance (NMR) spectrum of 1-chlorophthalazine that was prepared conventionally.
Figure 4:
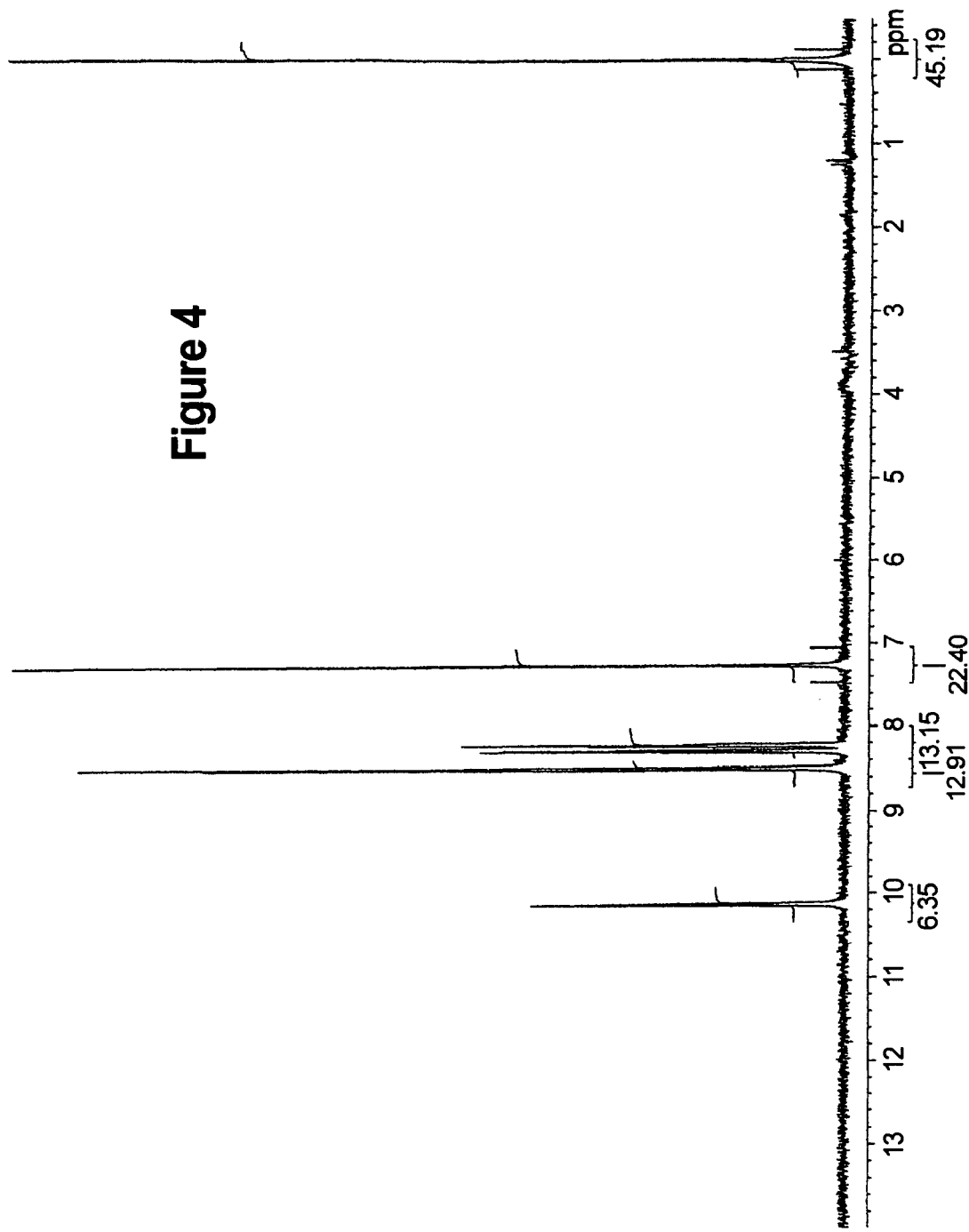
FIG. 4 is a $^1H$ nuclear magnetic resonance (NMR) spectrum of 1-chlorophthalazine that was prepared in accordance with the present invention.

The hydralazine hydrochloride solutions prepared in accordance with Examples 4–7 were stored inverted both at +25 and +40° C. Each solution was analyzed prior to packaging in the glass bottles and after two weeks and 4 weeks of storage. At each of these time intervals, the solutions were visually analyzed for color and visible particulate matter, and instrumentally by light obscuration for subvisible particulate matter having particles with a diameter of >10 microns and >25 microns. (see FIGS. 1 and 2)

After 118 days of storage, the solutions were visually analyzed for color and visible particulate matter, instrumentally by light obscuration for subvisible particulate matter having particles with a diameter of >10 microns and >25 microns, and by HPLC assay for hydralazine content, methylparaben content, and propylparaben content.

TABLE 2

Characteristics of Hydralazine Hydrochloride Solutions After 118 Days of Storage at +25° C.

| Tests | Example 4 | Example 5 | Example 6 | Example 7 |
|---|---|---|---|---|
| | | Observations | | |
| Visual Appearance | Clear & colorless | Clear & colorless | Clear & colorless | Clear, light yellow |
| Assay by HPLC | (As % of original value) | (As % of original value) | (As % of original value) | (As % of original value) |
| Hydralazine | 101.1% | 100.3% | 99.2% | 100.0% |
| Methyl paraben | Not present | 100.6% | 99.8% | 100.2% |
| Propyl paraben | Not present | 98.1% | 95.3% | 98.4% |
| Visible Particulate | None | None | None | None |

TABLE 3

Characteristics of Hydralazine Hydrochloride Solutions After 118 Days of Storage at +40° C.

| Tests | Example 4 | Example 5 | Example 6 | Example 7 |
|---|---|---|---|---|
| | | Observations | | |
| Visual Appearance | Clear & colorless | Clear & colorless | Clear & colorless | Clear, light yellow |
| Assay by HPLC | (As % of original value) | (As % of original value) | (As % of original value) | (As % of original value) |
| Hydralazine | 101.1% | 100.3% | 99.2% | 100.0% |
| Methyl paraben | Not present | 100.6% | 99.8% | 100.2% |
| Propyl paraben | Not present | 98.1% | 95.3% | 98.4% |
| Visible Particulate | None | None | None | None |
| Subvisual Particulate | (Per container) | (Per container) | (Per container) | (Per container) |
| >10 microns | 1210 | 2080 | 1770 | 2370 |
| >25 microns | 60 | 100 | 160 | 60 |

Example 10

Preparation of Stable Hydralazin Hydrochloride Pharmaceutical Composition.

A liquid pharmaceutical formulation for parenteral administration of hydralazine hydrochloride was prepared to contain 5 mg/mL hydralazine hydrochloride (prepared in Example 2), 0.325 mg/mL methyl paraben, 0.175 mg/mL propyl paraben, and 100 mg/mL propylene glycol or poly (ethylene glycol) in sterile water for injection. In addition, individual preparations were prepared to contain poly(ethylene glycol) (PEG) having an average molecular weight of 200, 400, 600, 1,000, 3,000, 5,000, or 10,000 Daltons (identified as "PEG-xxx"), each PEG meeting U.S. Pharmacopeial monograph standards for absence of ethylene oxide and ethylene glycol. Each formulation was packaged in a glass bottle containing either no metal or a strip of stainless steel metal ("SS") that was closed and sealed with an elasteomeric stopper.

Each formulation was observed for a period of 24 hours. Representative observations at 24 hours are presented in Table 4 unless a different time of observation is noted.

TABLE 4

Preparation of Stable Hydralazine Hydrochloride Pharmaceutical Composition.

| Formulation Containing | Solution Characteristics Post-Packaging (Time of Observation) | | | |
|---|---|---|---|---|
| | No Metal | SS304 | SS316 | SS316L |
| Propylene Glycol | Clear, colorless | Purple (<15 min.) | Purple (<15 min.) | Purple (<15 min.) |
| PEG-200 | Clear, colorless | Clear, colorless | Clear, colorless | Clear, colorless |
| PEG-400 | Clear, colorless | Clear, colorless | Clear, colorless | Clear, colorless |
| PEG-600 | Clear, colorless | Clear, colorless | Clear, colorless | Clear, colorless |
| PEG-1000 | Clear, colorless | Clear, colorless | Clear, colorless | Clear, colorless |
| PEG-3000 | Clear, colorless | Clear, colorless | Clear, colorless | Clear, colorless |
| PEG-5000 | Clear, colorless | Clear, colorless | Clear, colorless | Clear, colorless |
| PEG-10000 | Clear, colorless | Clear, colorless | Clear, colorless | Clear, colorless |
| PEG-20000 | Clear, colorless | Clear, colorless | Clear, colorless | Clear, colorless |

"Clear" refers to solutions containing no visible particulate matter or yellow precipitates.

The present invention has been described in detail using specific examples to illustrate the preferred embodiments of the invention. However, it will be obvious to those skilled in the art that various modifications thereto can be made without departing from the spirit and scope thereof.

I claim:

1. A method of preparing hydralazine hydrochloride, comprising the steps of:

a. heating a first mixture of 1-phthalazinone with phosphorous oxychloride thereby providing 1-chlorophthalazine;

b. contacting said 1-chlorophthalazine with an alkane comprised of from about 5 to about 7 carbon atoms;

c. removing said alkane from said 1-chlorophthalazine;

d. contacting said 1-chlorophthalazine obtained in step c with tetrahydrofuran;

e. removing said tetrahydrofuran from said 1-chlorophthalzine;

f. heating a second mixture containing 1-chlorophthalazine from step e and hydrazine hydrate thereby providing hydralazine;

g. separating said hydralazine from said second mixture;

h. contacting said hydralazine from step g with hydrochloric acid thereby providing hydralazine hydrochloride.

2. The method of claim 1 wherein said alkane is hexane.

3. The method of claim 1 wherein steps f through h are performed in vessels having a non-metallic contact surface.

4. The method of claim 1 wherein said first mixture is heated to a temperature from about 70° to about 85° C. for a time sufficient to convert 1-phthalazine to 1-chlorophthalazine.

5. The method of claim 1 wherein said 1-chlorophthalazine obtained from step e is a powder.

6. The method of one of claim 1 or 3 wherein the second mixture is prepared by adding 1-chlorophthalazine to said hydrazine prior to heating.

7. The method of one of claim 1 or 3 wherein said second mixture is heated to a temperature from about 60° to about 70° C. for a time sufficient to convert 1-chlorophthalazine to hydralazine.

8. The method of claim 1 wherein said alkane is hexane, said first mixture is heated to a temperature from about 70° to about 85° C. for a time sufficient to convert 1-phthalazine to 1-chlorophthalazine, said 1-chlorophthalazine obtained from step e is precipitated, the second mixture is prepared by adding 1-chlorophthalazine to said hydrazine prior to heating and said second mixture is heated to a temperature from about 60° to about 70° C. for a time sufficient to convert 1-chlorophthalazine to hydralazine.

9. A method of preparing hydralazine hydrochloride, comprising the steps of:
a. heating a first mixture of 1-phthalazinone with phosphorous oxychloride thereby providing 1-chlorophthalazine;
b. separating said 1-chlorophthalazine from said first mixture as a solid free flowing powder;
c. heating a second mixture containing 1-chlorophthalazine from step b and hydrazine hydrate thereby providing hydralazine;
d. separating said hydralazine from said second mixture; and
e. contacting said hydralazine from step d with hydrochloric acid thereby providing hydralazine hydrochloride.

10. The method of claim 9, wherein said 1-chlorophthalazine is separated in step b by precipitation.

11. A method of preparing a chlorinated heterocyclic compound having the formula:

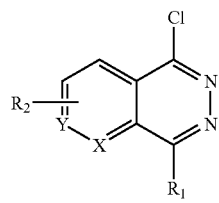

where X and Y are independently carbon or nitrogen, and $R_1$ and $R_2$ are independently selected from the group consisting of hydrogen, alkyl($C_1$–$C_6$), alkoxy, aryl heteroaryl;
comprising the steps of:
heating a first mixture of a compound having the formula:

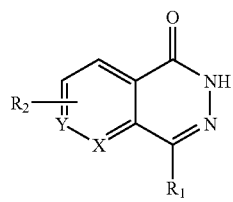

where X and Y are independently carbon or nitrogen, and $R_1$ and $R_2$ are independently selected from the group consisting of hydrogen, alkyl ($C_1$–$C_6$), alkoxy, aryl, and heteroaryl, with phosphorous oxychloride thereby providing an admixture containing said chlorinated heterocyclic compound;
contacting said mixture with an alkane comprised of from about 5 to about 7 carbon atoms; and
removing said alkane from said chlorinated heterocyclic compound.

12. A method of preparing a chlorinated heterocyclic compound having the formula:

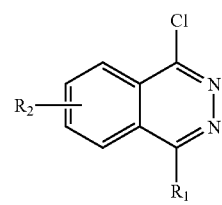

where $R_1$ and $R_2$ are independently selected from the group consisting of hydrogen, alkyl ($C_1$–$C_6$), alkoxy, aryl, heteroaryl; alkylaryl, aryloxy, and alkylaryloxy;
comprising the steps of:
heating a first mixture of a compound having the formula:

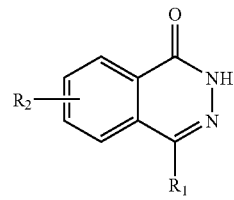

where $R_1$ and $R_2$ are independently selected from the group consisting of hydrogen, alkyl ($C_1$–$C_6$), alkoxy, aryl, and heteroaryl, alkylaryl, aryloxy, and alkylaryloxy, with phosphorous oxychloride thereby providing an admixture containing said chlorinated heterocyclic compound;
contacting said mixture with an alkane comprised of from about 5 to about 7 carbon atoms; and
removing said alkane from said chlorinated heterocyclic compound.

13. The method of claim 12 where $R_1$ and $R_2$ are hydrogen.

14. The method of one of claims 11, 12, or 13 wherein said chlorinated heterocyclic compound is powder.

* * * * *